United States Patent [19]

Castellini

[11] Patent Number: 5,044,952
[45] Date of Patent: Sep. 3, 1991

[54] DEVICE TO PREVENT WATER STAGNATION IN DENTAL SUPPLY CIRCUITS

[75] Inventor: Franco Castellini, Bologna, Italy
[73] Assignee: Castellini, S.p.A., Bologna, Italy
[21] Appl. No.: 429,359
[22] Filed: Oct. 31, 1989

[30] Foreign Application Priority Data

Nov. 11, 1988 [IT] Italy ............................ 3659 A/88
Mar. 24, 1988 [IT] Italy ............................ 3398 A/89

[51] Int. Cl.⁵ .............................................. A61C 1/10
[52] U.S. Cl. ........................................ 433/84; 433/98
[58] Field of Search .............................. 433/84, 80, 98

[56] References Cited

U.S. PATENT DOCUMENTS 3,035,349 5/1962 Reid et al. ............................. 433/84
3,169,318 2/1965 Oaks ...................................... 433/85
3,838,516 10/1974 Borochaner ........................... 433/84
4,545,956 10/1985 Ciszewski et al. ................... 422/28

FOREIGN PATENT DOCUMENTS 313527 4/1989 European Pat. Off. .

Primary Examiner—John J. Wilson
Attorney, Agent, or Firm—Leff, Whitesel, Conte & Saret

[57] ABSTRACT

The device consists in a variable restriction installed in conjunction with a chip blower, located between the warm water inlet and the return line connecting the relative handpiece to the main waste outlet, which is made to open continuously or intermittently, at least while the apparatus is in operation, so as to allow a moderate trickle of water through to the waste outlet and ensure that no stagnation occurs; the particular method of installing the restriction also permits of keeping the handpiece at a temperature near to that of the water supplied through the inlet, even when the blower is not actually in use.

5 Claims, 2 Drawing Sheets 5,044,952

DEVICE TO PREVENT WATER STAGNATION IN DENTAL SUPPLY CIRCUITS

BACKGROUND OF THE INVENTION

The present invention relates to a device designed to prevent the stagnation of water in the supply pipelines of medical equipment, and in particular, of dental surgery apparatus.

A possible source of contamination threatening each power driven instrument connected to a conventional dental surgery apparatus is represented by the water used in operation of the apparatus.

Whilst it is true that the domestic water supply, being potable, is not a carrier of micro-organisms in any significant quantity, it is equally true that there are conditions in which this same water is caused to linger and stagnate for considerable periods of time, both in the permanent pipework of the surgery's plumbing system and in the spray and replenishing circuits of the apparatus.

Stagnation, it is known, has the effect of raising the overall quantity of micro-organisms in water, even drinking water, to levels that can no longer be considered safe.

The microbiological content produced by stagnation poses no significant threat where drinking water is merely swallowed by a patient; in the particular instance of dental surgery, however, where water is supplied to surgical instruments and/or to power driven handpieces or other appliances associated with the apparatus, the micro-organisms generated by stagnation are inevitably brought into contact with exposed body tissue, with the result that infection can occur, occasioning prolonged healing time, inflammation, increased levels of pain post-treatment, and fever in more serious cases.

Certain remedies involve dispensing a disinfectant continuously into the water supply circuits, though with the consequent drawbacks that the construction of the apparatus is rendered more complex, and the properties of the liquid are affected.

The object of the invention is to provide a device that will prevent stagnation of water in the supply circuits of dental surgery apparatus, ultimately inhibiting the proliferation of micro-organisms, doing so without the use of additional substances; a further object of the invention is to enable a substantially instantaneous supply of warm water to those instruments which utilize feed and return flow in conjunction with a built-in on-off control, for example chip blowers.

SUMMARY OF THE INVENTION

The stated objects are fully realized according to the present invention, which consists essentially in installing a variable flow valve or restriction on the drinking water inlet to the replenishing and spray circuits of dental surgery apparatus, which by allowing a trickle of water through to the waste outlet is able to prevent stagnation.

Besides being extremely simple in construction and operation, this expedient also affords the signal advantage that no chemical product whatsoever is mingled with the potable water supply; accordingly, the chemical and physical properties of the water remain unaffected, and there is no possibility of either patient or practitioner being invested by atomized disinfectant.

BRIEF DESCRIPTION OF THE DRAWINGS

The invention will now be described in detail, by way of example, with the aid of the accompanying drawings, in which.

DESCRIPTION OF THE PREFERRED EMBODIMENTS

Figure 1:
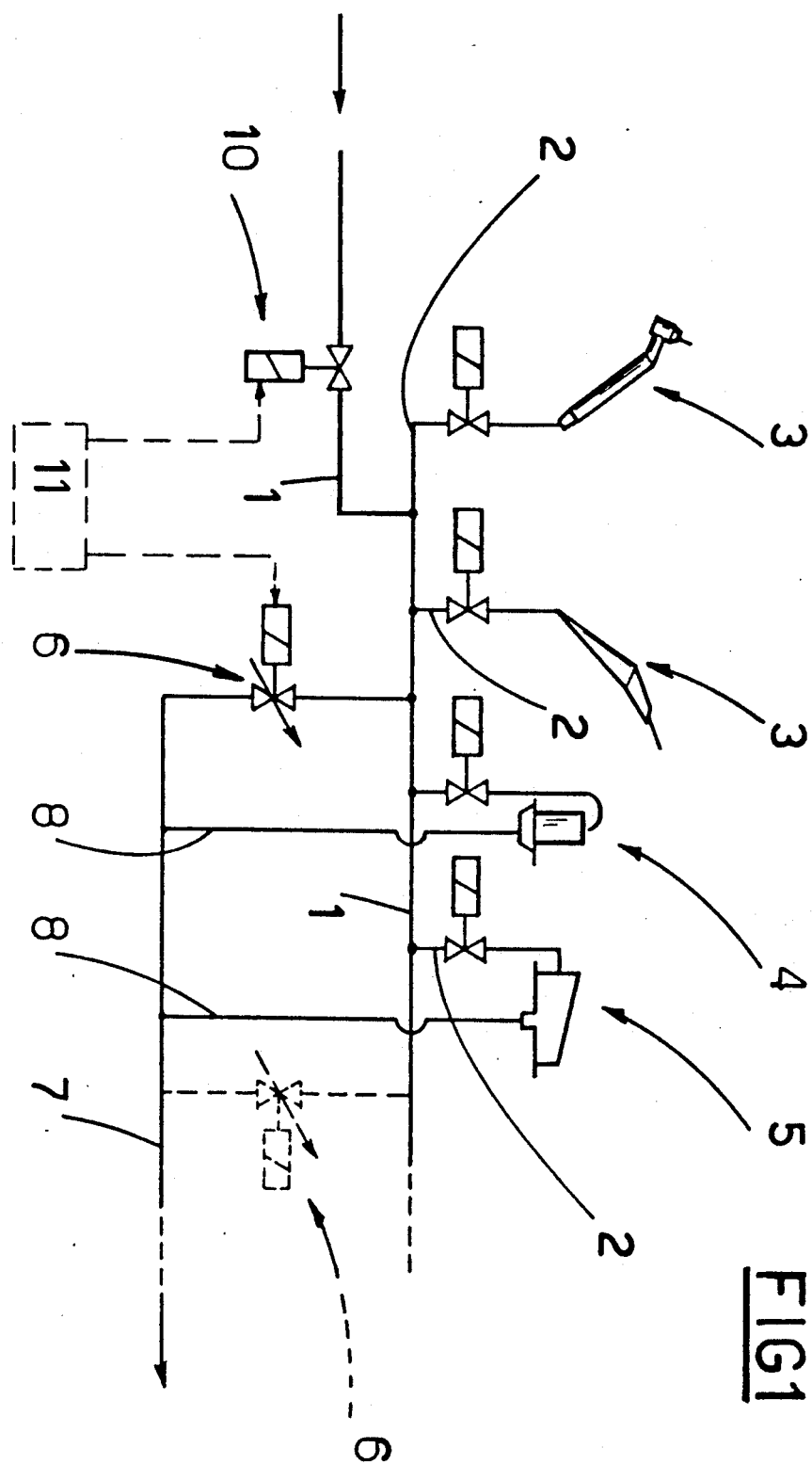
FIG. 1 shows the schematic circuit diagram of a system according to the invention in a general form of application.

With reference first to FIG. 1, which schematically illustrates a possible embodiment for the potable water supply circuit constituting part of a dental surgery apparatus, 1 denotes a main inlet pipeline controlled by a main on-off valve 10, from which a number of branches 2 are taken off and routed to the handpieces of power driven instruments 3, to the replenishing outlet for an oral rinse drinking glass 4, and to a spittoon cup 5, the latter two connecting by way of respective waste pipes 8 with a main waste outlet 7 from the apparatus.

In the example of FIG. 1, the device according to the invention consists essentially in variable flow bleed-off means 6, embodied in practice as a valve connecting with the main inlet 1 on the one hand, and on the other, with the main waste outlet 7. More exactly, the valve 6 connects with the inlet 1 at a point downstream of the branch 2 to the last instrument 3 in line.

Needless to say, the same result is obtainable with the point of connection between valve 6 and inlet 1 differently located, for example, downstream of the branch to the spittoon 5 (see phantom line, FIG. 1). The valve 6 might be operated manually, or in a preferred embodiment, interlocked to the means by which the apparatus is switched on in such a way as to activate automatically.

The flow passage of the valve 6 will be calibrated, clearly enough, in such a way that the steady bleed of water from the inlet line is kept small enough to contain consumption, and at the same time, to ensure that the supply to the instruments remains unaffected.

Figure 2:
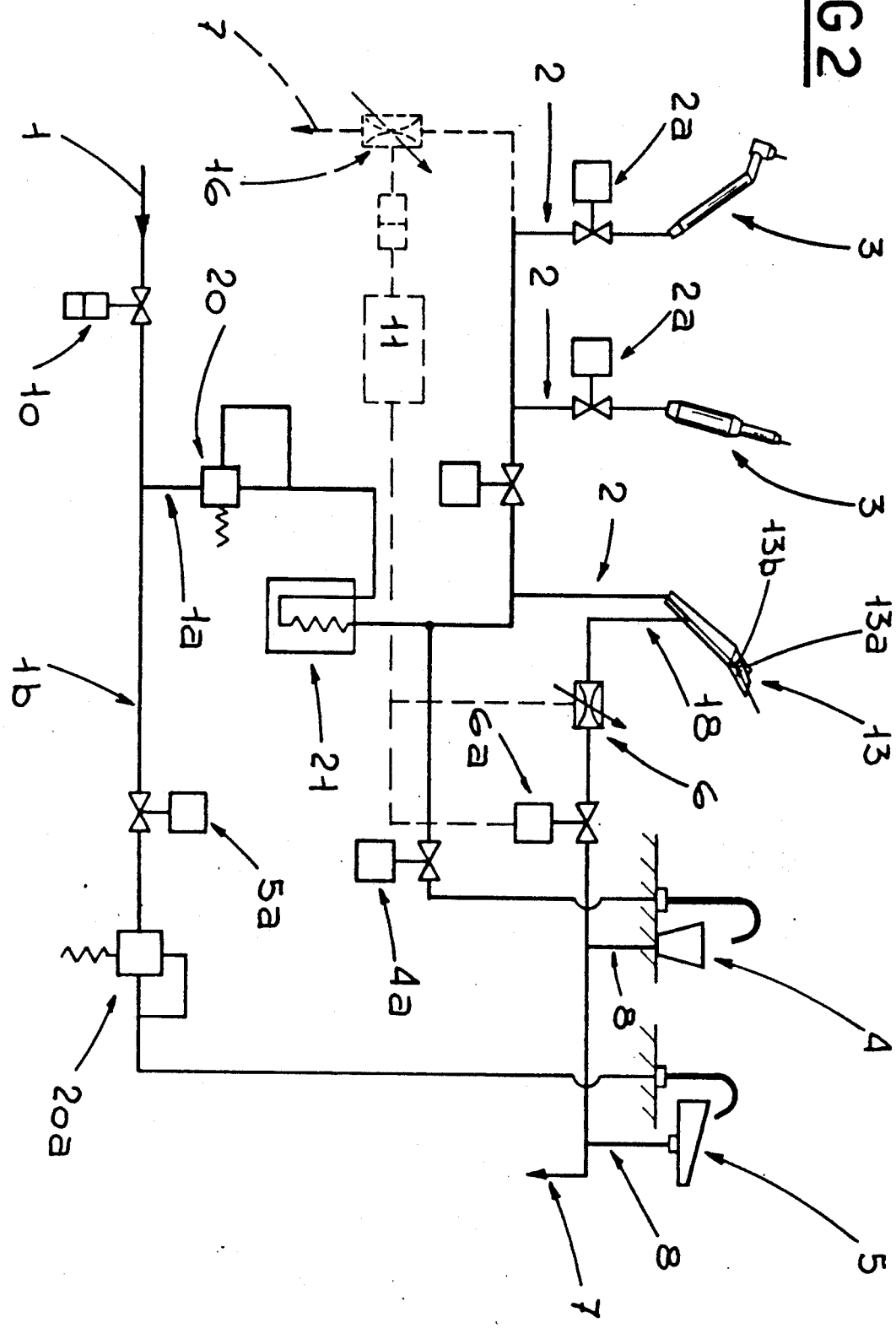
FIG. 2 is a diagram illustrating integration of the device disclosed into dental surgery apparatus.

With reference to FIG. 2, which also illustrates a typical method of supplying potable water to a conventional apparatus, the main inlet line 1 is controlled by a main valve 10 as in FIG. 1, and will be seen to divide into first and second circuits 1a and 1b; the first circuit 1a is connected initially to a first pressure reducing valve 20, downstream of which the water passes into a heater 21, then to the branches 2 supplying the handpieces 3 (each controlled by a relative on-off valve 2a), the chip blower 13 and the oral rinse outlet 4, whereas the second circuit 1b supplies the spittoon 5, by way of a second pressure reducing valve 20a.

The chip blower 13 is of a general type provided with its own independent control, in the form of a button 13a and an on-off valve 13b incorporated into the handle. The oral rinse 4 and spittoon 5 stations are connected by respective waste lines 8 to the main waste outlet 7, and their relative water supply circuits controlled by conventional valves denoted 4a and 5a.

In the example of FIG. 2, the device according to the invention consists in:

a variable flow restriction 6 (or bleed-off means, one for each blower 13 in the event of there being more than one fitted) located on a return line 18 departing from the blower 13, connected permanently to the relative supply branch 2, and discharging through the relative waste line 8 into the main waste outlet 7; and a valve 6a located immediately downstream of the restriction 6 and functioning as a shut-off.

Once again, the valves 6 and 6a in question can be operated manually, or preferably, interlocked to the power switch of the apparatus and activated automatically.

Adopting this expedient, it becomes possible to maintain a continuous trickle of running water along the entire length of the inlet line, and most especially, through the stretch branching off to the handpieces 3 and the rinse glass 4; whilst the flow generated will be limited, it is nonetheless sufficient to prevent stagnation occurring in the water lines and around the various valves, whether directly or indirectly invested. With the bleed-off means 6 installed on the return line 18 from the chip blower 13, it becomes possible, by virtue of the blower's mechanical embodiment, to maintain a steady flow of water through the blower handpiece: thus, not only is stagnation prevented, but the instrument 13 can be maintained at a temperature corresponding essentially to that generated by the heater 21, so that when activated, water will be ejected substantially at body temperature rather than cold; the closer the proximity of the on-off valve 13b and the entry to the return line 18, the more pronounced this effect will be.

In FIG. 2, the shut-off valve 6a differs from the restriction 6 inasmuch as the trickle can be halted completely in the event that the blower and the other handpieces are to be flooded with a liquid other than water, say, a physiological solution, which if allowed to drain continuously would be consumed too quickly.

Whilst the expedient thus described is certainly the most simple from the standpoint of economy in component parts, the alternative also exists of installing a second variable flow restriction 16, identical to the first 6, connected to the first circuit 1a (downstream of the heater 21) on the one hand, and on the other, to the main waste outlet 7. Given the simple conception of the device, use can be made of means, programmable on the part of the user and integrated into the control systems of the apparatus as a whole, designed to pilot a timer forming part of monitoring and control circuits 11 by which the main valve 10 and the trickle valve 6 (or valves 6 and 16) are caused to open at a set time prior to the commencement of surgery hours, and thus drain away the water that will have been stagnating during the 'off' interval (nocturnal in particular).

Whilst reference is made in the foregoing text to valves and restrictions of variable flow design, such components could be replaced by others capable of performing the equivalent function, or in any event, of inducing and controlling a trickle of liquid from the pipelines in question. Similarly, the valve or restriction 6 (and 16) could be left permanently open, or operated intermittently; in either instance, the end remains one of ensuring a prolonged, stagnation-preventing bleed-off.

What is claimed is:

1. A device serving to prevent stagnation of water in supply circuits of dental surgery apparatus having a potable water inlet line and a main waste outlet, comprising at least a variable flow bleed-off means connected between said potable water inlet line and said main waste outlet, said bleed-off means being opened continuously when the apparatus is in the operative phase to provide a constant and moderate trickle of water through to the main waste outlet, said potable water inlet line serving:

a first circuit having heating means to supply heated water to a branch handpiece line, to a chip blower of the type in continuous receipt of water from said inlet line, affording a handpiece built-in on-off valve and connected by way of a return line to said main waste outlet, and to an oral rinse glass replenishing outlet;

a second circuit supplying water at least to a spittoon cup;

wherein said bleed-off means is a variable flow restriction installed on the said chip blower return line in such a way as to bring a continuous connection between the relative supply inlet line and said main waste outlet and thus obtaining a heated running water flow through said blower handpiece;

a valve installed downstream of said variable flow restriction and serving to shut off the flow of water through the return line without altering the current setting of said restriction; and wherein said bleed-off means comprise further a bleed-off valve installed on said branch handpiece line and consisting in a variable flow restriction the purpose of which is to bring a continuous connection between the branch handpieces line and the main waste outlet, in such a way as to ensure the constant and moderate trickle of water through to the main waste outlet.

2. A device as in claim 1, wherein said bleed-off means is a variable flow valve installed on the potable water inlet line.

3. A device as in claim 1, wherein said potable water inlet line serves a plurality of branches carrying potable water to handpieces, to an oral rinse glass replenishing outlet, and to a spittoon cup, said variable flow valve is installed on the potable water inlet line downstream of the branches serving the handpieces.

4. A device as in claim 1, associated with dental surgery apparatus in which the potable water inlet line is controlled by a main on-off valve, comprising means, embodied and operating independently of a main apparatus control system, able to monitor and control said variable flow bleed-off means and said main on-off valve.

5. A device as in claim 1, associated with dental surgery apparatus in which the potable water inlet line is controlled by a main on-off valve, comprising means, embodied and operating independently of a main apparatus control system, able to monitor and control said variable flow bleed-off means and said main on-off valve.

* * * * *